United States Patent
Hilaly et al.

(10) Patent No.: US 7,524,526 B2
(45) Date of Patent: Apr. 28, 2009

(54) PROCESS FOR PRODUCING HIGH PURITY ISOFLAVONES

(75) Inventors: Ahmad K. Hilaly, Springfield, IL (US); Bob Sandage, Decatur, IL (US); John Soper, Mt. Zion, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 10/409,683

(22) Filed: Apr. 9, 2003

(65) Prior Publication Data

US 2004/0019226 A1    Jan. 29, 2004

Related U.S. Application Data

(60) Provisional application No. 60/371,129, filed on Apr. 10, 2002.

(51) Int. Cl.
  *A23J 1/00* (2006.01)
(52) U.S. Cl. .................. 426/656; 426/634; 426/422; 426/423; 426/442
(58) Field of Classification Search .......... 426/656, 426/634
  See application file for complete search history.

(56) References Cited

U.S. PATENT DOCUMENTS

| | | | | |
|---|---|---|---|---|
| 3,721,569 | A | * | 3/1973 | Steinkraus ............ 426/430 |
| 4,157,984 | A | | 6/1979 | Zilliken |
| 4,172,828 | A | | 10/1979 | Davidson et al. |
| 4,234,577 | A | | 11/1980 | Zilliken |
| 4,390,559 | A | * | 6/1983 | Zilliken ............ 426/545 |
| 5,670,632 | A | * | 9/1997 | Chaihorsky ............ 536/8 |
| 5,679,806 | A | | 10/1997 | Zheng et al. |
| 5,702,752 | A | | 12/1997 | Gugger et al. |
| 5,792,503 | A | | 8/1998 | Gugger et al. |
| 5,919,921 | A | | 7/1999 | Waggle et al. |
| 6,033,714 | A | * | 3/2000 | Gugger et al. ............ 426/634 |
| 6,228,993 | B1 | | 5/2001 | Konwinski |
| 6,320,028 | B1 | | 11/2001 | Konwinski |
| 2004/0121059 | A1 | | 6/2004 | Singh |

FOREIGN PATENT DOCUMENTS

| JP | 7-70170 | * | 3/1995 |
|---|---|---|---|
| JP | 407070170 | | 3/1995 |

OTHER PUBLICATIONS

Derwent Abstract of Japanese Patent No. JP 05-170756, Accession No. 1993-252721.
Mitsubishi Chemical Corporation website http://www.diaion.com/Sepabeads_Tables/Sepabeads_Guide_R_E.htm (visited Nov. 3, 2005).
Amersham Biosciences website http://www.chromatography.amershambiosciences.com/aptrizz/upp00919.nsf/content/E8E... (visited Oct. 31, 2005).
Kramer, R., et al., *Antifungal activity of Soybean and Chickpea Isoflavones and Their Reduced Derivatives*, Phytochemistry, vol. 23, No. 10, pp. 2203-2205 (1984).
Jha, Chandra H., et al. *Inhibition of Invitro Microsomal Lipid Peroxidation by Isoflavonoids*, Biochemical Phamacology, vol. 34, No. 9, pp. 1367-1369 (1985).
Wolfbeis, O., et al., *The Absorption and Fluorescence of Isoflavones and the Effect of Shift Reagents*, Z Naturforsch, 39b, pp. 238-243 (1984).

* cited by examiner

*Primary Examiner*—Anthony Weier
(74) *Attorney, Agent, or Firm*—K&L Gates LLP

(57) ABSTRACT

A process for the production of a high purity isoflavone composition is disclosed. The process involves subjecting plant material to a primary chromatographic step to obtain an isoflavone enriched fraction and subjecting the isoflavone enriched fraction to a secondary chromatographic step. Also disclosed is a process that involves passing the plant material through an ultrafiltration membrane which has a molecular weight cut-off range that produces a plant material permeate prior to subjecting the plant material permeate to primary and secondary chromatographic steps.

18 Claims, No Drawings

PROCESS FOR PRODUCING HIGH PURITY ISOFLAVONES

CROSS REFERENCE TO RELATED APPLICATIONS

This application claims benefit of U.S. Provisional Application No. 60/371,129, filed Apr. 10, 2002, which is incorporated herein by reference in its entirety.

BACKGROUND OF THE INVENTION

1. Field of the Invention

The present invention relates to a process for producing high purity isoflavones. More particularly, the present invention relates to a process for producing high purity isoflavones by a process combining primary and secondary chromatographic steps.

2. Related Art

Isoflavones are a class of plant flavonoid compounds which have estrogenic activity. Research has revealed many possible health benefits that may be achieved from the consumption of isoflavones. High cholesterol is believed to contribute to the development of coronary heart disease and isoflavones have been demonstrated to lower cholesterol in animal studies. Isoflavones may also play a role in preventing certain types of cancer. Bone loss in women during and after menopause may also be prevented or ameliorated by isoflavones. Because of these and other potential health effects, the commercial demand for isoflavones is expected to rise rapidly.

There are a few processes already reported for isoflavone purification. U.S. Pat. No. 5,679,806 describes a process for purifying isoflavones from soy molasses by complicated chromatography and crystallization steps. U.S. Pat. No. 5,919,921 describes a process for purifying isoflavones from soy molasses by precipitation and drying. U.S. Pat. No. 5,670,632 describes a process based on chromatography using strong cation exchange resins. U.S. Pat. No. 6,320,028 describes a process for making an isoflavone product from soybeans based on extraction and precipitation. All of these reported processes are too cumbersome for the production of isoflavones on an industrial scale. Also, these processes are unable to make a high purity product. In fact, the typical purity level associated with these methods is only in the 4% to 50% range. For example, while the process disclosed in U.S. Pat. No. 6,033,714 produces an excellent isoflavone product from soy molasses, the product is typically from about 30% to about 50% isoflavones on a dry solids basis. Therefore, there is a great need for improved processes that can provide very high purity isoflavone products.

SUMMARY OF THE INVENTION

The present invention provides a simple and effective method to produce high purity isoflavones from soy solubles. Specifically, the present invention provides a process for producing high purity isoflavone fractions from a plant starting material, said process comprising the steps of subjecting the plant material to a primary chromatographic step to obtain an isoflavone enriched fraction and subjecting the isoflavone enriched fraction to a secondary chromatographic step. The present invention also provides a process for producing high purity isoflavone fractions from a plant material comprising the step of passing the plant material through an ultrafiltration membrane which has a molecular weight cut-off range that produces a plant material permeate and subjecting the plant material permeate to a primary chromatographic step to obtain an isoflavone enriched fraction and subjecting the isoflavone enriched fraction to a secondary chromatographic step.

The present invention also provides a process for separating high purity isoflavone fractions from an aqueous plant starting material, said process comprising the steps of heating an aqueous plant starting material to a constant temperature selected on a basis of an aqueous solubility for at least one desired isoflavone fraction that is to be recovered; passing the heated staffing material through an ultrafiltration membrane to obtain a plant material permeate, the membrane having a cut-off which passes at least one isoflavone fraction; treating the permeate with an adsorptive material; washing the adsorptive material in water; eluting at least one adsorbed isoflavone fraction from the water-washed adsorptive material with aqueous alcohol to obtain an isoflavone enriched fraction; subjecting the isoflavone enriched fraction to a secondary chromatography with an adsorptive material; eluting with one or more series of at least one bed volume of aqueous alcohol, at least one isoflavone fraction from the secondary chromatography; and evaporating the aqueous alcohol from a stream used during the elution in order to promote the crystallization of at least one isoflavone fraction.

The various objects and advantages of the present invention will be clear from the description that follows.

DETAILED DESCRIPTION OF THE INVENTION

The process of the present invention uses the soluble fraction of soy materials that results from the processing of soybeans to make soy protein concentrate. U.S. Pat. No. 4,172,828 contains a detailed discussion of a method for processing soy protein from defatted soybean flakes, and U.S. Pat. Nos. 5,702,752; 5,792,503; and 6,033,714 disclose further details of further processing of the soy solubles, also known as soy molasses. Soy solubles, or molasses, is the alcohol-stripped extract that results from aqueous ethanol extraction of hexane defatted soybean flakes.

While the process disclosed in U.S. Pat. No. 6,033,714 provides an excellent product with an isoflavone content in dried material produced from soy molasses of from about 30% to about 50% on a dry solids basis, the inventors of the present invention have surprisingly discovered that a process utilizing a primary and then a secondary chromatographic step, will produce a high purity isoflavone enriched fraction that has a purity in a range of about 70% to about 100%. The inventors of the present invention have also surprisingly discovered that a process utilizing an ultrafiltration step followed by a primary and then a secondary chromatographic step, will produce a high purity isoflavone enriched fraction that has a purity in a range of about 70% to about 95%. The inventors of the present invention have also surprisingly discovered that a process utilizing an ultrafiltration step followed by a primary and then a secondary chromatographic step, will produce a high purity isoflavone enriched fraction that has a purity in a range of about 80% to about 95%.

The inventors of the present invention have also surprisingly discovered that a process utilizing an ultrafiltration step followed by a primary and then a secondary chromatographic step, will, after evaporation and drying of the product fraction from the secondary chromatographic step, produce a greater than 90% pure isoflavone product.

Soy solubles, or soy molasses, is first pH adjusted to a pH of from about 4 to about 10, preferably from about 4.5 to about 9.5, most preferably from about 5 to about 9. As those of skill in the art will recognize, the optimum pH of this material will depend in large part upon the requirements of the relative amounts of the types and forms of specific isoflavones desired in the final product. The temperature of the material must also be adjusted, in large part for the same reasons, and is typically within the range of from about 40° C. to about 100° C., preferably from about 50° C. to 95° C., most preferably about 60° C. to about 95° C. The molecular weight cut-off (MWCO) of the ultrafiltration membrane can vary, typically anywhere from about 600 to about 1,000,000 but a preferred MWCO is about 100,000. Alternatively, the membrane can be selected on the basis of pore size, with about 0.1 micron a preferred size. (See U.S. Pat. No. 6,033,714). The ultrafiltration system should be set up to run at optimum transmembrane pressure, and in preferred embodiments a diafiltration feed is provided in order to recover a greater percentage of isoflavones in the permeate.

This ultrafiltration permeate is then subjected to a primary chromatography step. The chromatography may be either batch or continuous, and any number of chromatographic resins may be employed in the process of the present invention. U.S. Pat. No. 6,033,714 lists useful resin types and discusses "Amberlite" XAD-4 specifically. The anionic adsorbent resin TULSION A-2X MP (Thermax Inc., Novi, Mich.) is another useful resin for the practice of the present invention. The pH and temperature of this feed are adjusted to a pH of from about 5 to about 10, more preferably from about pH 5.5 to about 9.0, and the temperature of the column can be regulated as necessary and appropriate, using the proper column design and equipment. As above, the temperature is typically within the range of from about 60° C. to about 95° C. As those of skill in the art will recognize, column size and design will depend in large part upon the amounts of materials being fed and produced, and can vary widely.

In addition, of course, the column design and the choice of resin will dictate, in part at least, the parameters used in running the chromatography (for example the number of rinses, and the number of bed volumes of alcohol used to elute the isoflavones from the column). Rinsing of the column is typically performed with deionized water; isoflavones are typically eluted from resins such as those used in the practice of the present invention using aqueous alcohol. For example, ethanol, methanol, or isopropanol may be used, with a preferred percentage of alcohol of from about 65% to about 100%, and more preferred from about 67% to about 95%, and even more preferred from about 70% to about 90%. An alcohol gradient process for elution may also be employed.

The elution product from this primary chromatography is then subjected to a secondary chromatography. Similar resins can be employed; specific resins found to be useful in the practice of this secondary chromatography include, for example, the non-ionic adsorbent resin TULSION ADS 600 (Thermax Inc., Novi, Mich.), DOW OPTIPORE SD-2 (Dow Chemical, Midland, Michigan), DOW OPTIPORE XUS 40325 (Dow Chemical, Midland, Mich.), and Rohm & Haas XAD 1600 or Rohm & Haas XAD 7HP resins. As is the case with regard to the primary chromatography, the pre-treatment of the resin chosen for the secondary chromatography will be dictated in large part by the manufacturer's specifications, and by the relative amounts of the various forms and types of isoflavones desired in the final product. Furthermore, as above, the pH and temperature of the feed will be adjusted for the same reasons. Also, the number of bed volumes of wash water and eluent will also be a matter of choice and process parameter optimization well within the ordinary skill in the art given the instant disclosure. Again, aqueous alcohols are the preferred eluents for the practice of the present invention. In certain embodiments, a double elution is practiced; the first using a lower alcohol concentration (from about 30% to about 50%), the second using a higher alcohol concentration (from about 65% to about 80%).

After the elution(s) from the secondary chromatography, the recovered fraction(s) may be evaporated and dried. Evaporation can be accomplished by any of a number of art-recognized methods, including, for example, a multi-effect evaporator. Drying is also accomplished by any number of art-recognized methods, including, for example, spray drying, freeze drying, and the like. A preferred method for drying is spray drying.

EXAMPLE 1

Primary Chromatography

Experiments were carried out in a jacketed glass column containing 100 mls of an anionic adsorbent resin (in this case TULSION A-2X MP). The temperature of the column was maintained at 60-65° C. by circulating hot water through the jacket of the column. The resins were conditioned by running 3 bed volumes (300 mls) of a solution of 2.5% NaOH through the resin. The resins were then rinsed with 3 bed volumes of deionized water. The flow rate for all steps in these tests was 12 mls/min. Ultra-filtration permeate, obtained from ADM Nova Soy plant, was used as feed in these tests. The pH of the feed material was 5.5. This feed material (1.5 liters) was then pumped through the resin. Then 3 bed volumes of deionized water was run through the column. After the rinse, 5 bed volumes (500 mls) of a solution of 90% ethanol was pumped through the resin. The effluent was sampled and collected as PRODUCT. The results from this operation appear below:

| SAMPLE | Isoflavones (mg/Kg) | Dry Solids (g/Kg) | Purity | Yield |
|---|---|---|---|---|
| FEED | 1020.3 | 57.5 | 1.8 | |
| PRODUCT | 4147.9 | 7.3 | 57.1 | 81.31 |

EXAMPLE 2

Primary Chromatography

This experiment was the similar to that described in Example 1 with the following exceptions:
 1. Feed material was pH adjusted to 8.6.
 2. Feed volume was 20 bed volumes.
 3. Ethanol solution was of 70% concentration.

The results from this operation appear below:

| SAMPLE | Isoflavones (mg/Kg) | Dry Solids (g/Kg) | Purity (%) | Yield (%) |
|---|---|---|---|---|
| FEED | 544.9 | 47.1 | 1.2 | |
| PRODUCT | 857.4 | 1.4 | 63.0 | 78.7 |

EXAMPLE 3

Primary Chromatography

This experiment was the similar to that described in Example 2 with the following exceptions:

1. Feed material was pH adjusted to 9.0.
2. Resin used was ROHM & HAAS XAD4.

The effluent streams from this operation appear below:

| SAMPLE | Isoflavones (mg/Kg) | Dry Solids (g/Kg) | Purity (%) | Yield (%) |
| --- | --- | --- | --- | --- |
| FEED | 1773.7 | 203.7 | 0.9 | |
| PRODUCT | 5476.7 | 10.8 | 50.9 | 77.2 |

EXAMPLE 4

Secondary Chromatography

Experiments were carried out in a jacketed glass column containing 100 mls of non-ionic adsorbent resin (in this case TULSION ADS 600). The temperature of the column is maintained at 60-65° C. by circulating hot water through the jacket of the column. The resins were conditioned by running 3 bed volumes (300 mls) of a solution of 2.5% NaOH through the resin. The resins were then rinsed with 3 bed volumes of deionized water. The flow rate for all steps in this test was 12 mls/mm. Ethanol elution product made by the primary chromatography was used as the starting feed in these tests. This feed was diluted with water and the pH was adjusted to 9.3. One liter of this feed material was then passed through the resin bed. Then 3 bed volumes of deionized water was passed through the column. After the rinse, 5 bed volumes (500 mls) of a solution of 35% ethanol was passed through the resin. The effluent was sampled and collected as PROD. FRAC1. Then 5 bed volumes of a solution of 70% ethanol was passed through the column. The eluted volume was collected as PROD. FRAC2. The results are indicated below:

| SAMPLE | Isoflavones (mg/Kg) | Dry Solids (g/Kg) | Purity (%) | Yield (%) |
| --- | --- | --- | --- | --- |
| FEED | 785.1 | 1.6 | 49.1 | |
| PROD. FRAC1 | 1804.9 | 1.9 | 95.0 | 97.3 |
| PROD. FRAC2 | 6.7 | 0.0 | 100.0 | 0.4 |

EXAMPLE 5

Secondary Chromatography

This experiment was similar to that described in Example 4 with the following exceptions:
1. 5 bed volumes (500 mls.) of 35% ethanol (isocratic elution) were used.

The results from this operation appear below:

| SAMPLE | Isoflavones (mg/Kg) | Dry Solids (g/Kg) | Purity (%) | Yield (%) |
| --- | --- | --- | --- | --- |
| FEED | 785.1 | 1.6 | 49.1 | |
| PROD. FRAC1 | 1563.6 | 1.6 | 97.7 | 100.6 |

EXAMPLE 6

Secondary Chromatography

This experiment was similar to that described in Example 4 with the following exceptions:
1. Resin used was DOW OPTIPORE SD-2.
2. Feed volume through column was 20 bed volumes.

The effluent streams from this operation appear below:

| SAMPLE | Isoflavones (mg/Kg) | Dry Solids (g/Kg) | Purity (%) | Yield |
| --- | --- | --- | --- | --- |
| FEED | 692.8 | 1.9 | 36.5 | |
| PROD. FRAC1 | 1501.2 | 2.6 | 57.7 | 57.0 |
| PROD. FRAC2 | 1187.7 | 1.2 | 99.0 | 45.1 |

EXAMPLE 7

Secondary Chromatography

This experiment was similar to that described in Example 4 with the following exceptions:
1. Resin used was DOW OPTIPORE XUS 40325.
2. Feed volume through column was 20 bed volumes.

The results from this operation appear below:

| SAMPLE | Isoflavones (mg/Kg) | Dry Solids (g/Kg) | Purity | Yield (%) |
| --- | --- | --- | --- | --- |
| FEED | 903.9 | 2.1 | 43.0 | |
| PROD. FRAC1 | 1889.7 | 3.0 | 63.0 | 52.3 |
| PROD. FRAC2 | 1166.0 | 1.2 | 97.2 | 32.3 |

EXAMPLE 8

Secondary Chromatography

This experiment was similar to that described in Example 4 with the following exceptions:
1. Resin used was ROHM & HAAS XAD 1600.
2. Feed volume through column was 19 bed volumes.

The effluent streams from this operation appear below:

| SAMPLE | Isoflavones (mg/Kg) | Dry Solids (g/Kg) | Purity | Yield (%) |
| --- | --- | --- | --- | --- |
| FEED | 1067.9 | 1.6 | 66.7 | |
| PROD. FRAC1 | 3759.6 | 4.2 | 89.5 | 92.7 |
| PROD. FRAC2 | 360.4 | 0.4 | 90.1 | 8.8 |

EXAMPLE 9

Secondary Chromatography

This experiment was similar to that described in Example 4 with the following exceptions:
1. Resin used was ROHM & HAAS XAD 7HP.
2. Feed volume through column was 20 bed volumes.

The effluent streams from this operation appear below:

| SAMPLE | Isoflavones (mg/Kg) | Dry Solids (g/Kg) | Purity | Yield |
|---|---|---|---|---|
| FEED | 981.8 | 2.0 | 49.1 | |
| PROD. FRAC1 | 2866.4 | 5.0 | 57.3 | 73.0 |
| PROD. FRAC2 | 701.7 | 1.0 | 70.2 | 17.9 |

EXAMPLE 10

Ultra-Filtration

Soy solubles from ADM Soy Protein Concentrate plant were used as the staring material for isoflavones purification. 31 liters of this feed material were pH adjusted to 9.3 and heated to 77° C. This material was then ultra-filtered using a 100,000 MWCO polymeric membrane until there was 6 liters of retentate left in the feed tank. The filtration system was run in such a way as to maintain a 22-24 p.s.i. transmembrane pressure. Deionized water was added to the feed tank to a volume of 31 liters. This diafiltration feed was then run through the same system until there was 6 liters of retentate left in the tank. The recorded components of the resulting streams are indicated below:

| SAMPLE | Isoflavones (mg/Kg) | Dry Solids (g/Kg) | Purity (%) | Yield (%) |
|---|---|---|---|---|
| FEED | 1111.5 | 83.0 | 1.34 | |
| PERMEATE | 725.5 | 65.0 | 1.12 | |
| DIAPERMEATE | 352.4 | 20.0 | 1.76 | 78.2 |
| RETENTATE | 1067.2 | 108.0 | 0.99 | |

Having now fully described the present invention in some detail by way of illustration and example for purposes of clarity of understanding, it will be obvious to one of ordinary skill in the art that the same can be practiced by modifying or changing the invention with a wide and equivalent range of conditions, formulations and other parameters thereof, and that such modifications are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated herein by reference.

What is claimed is:

1. A process for producing a high purity isoflavone enriched fraction, the process comprising:
   crushing or grinding soybeans;
   removing oil from the crushed or ground soybeans, thus producing defatted soybean flakes;
   mixing the defatted soybean flakes with an alcohol, thus producing a liquor;
   separating a curd from whey of the liquor, thus producing soy solubles;
   subjecting the soy solubles to a chromatographic process consisting essentially of:
      placing the soy solubles in contact with an ionic resin, thus producing an isoflavone enriched fraction;
      eluting the isoflavone enriched fraction from the ionic resin;
      placing the isoflavone enriched fraction in contact with a non-ionic resin, thus producing the high purity isoflavone enriched fraction having a purity in a range of 70% to 100%; and
      eluting the high purity isoflavone enriched fraction from the non-ionic resin;
   wherein the isoflavones in the high purity isoflavone enriched fraction originate from the soybeans.

2. The process of claim 1, wherein the high purity isoflavone enriched fraction has a purity in a range of 70% to 95%.

3. The process of claim 2, wherein the high purity isoflavone enriched fraction has a purity in a range of 80% to 95%.

4. The process of claim 3, wherein the high purity isoflavone enriched fraction has a purity of 90%.

5. The process of claim 1, wherein the soy solubles are aqueous.

6. The process of claim 1, wherein the soy solubles are selected from the group consisting of soy molasses and soy whey.

7. The process of claim 1, further comprising heating the soy solubles.

8. The process of claim 7, wherein the temperature of the heat is in a range of 65° C. to 95° C.

9. The process of claim 1, further comprising ultrafiltering the soy solubles.

10. The process of claim 9, wherein the soy solubles are in a range of 600 to 1,000,000 MW.

11. The process of claim 10, wherein the soy solubles are less than 100,000 MW.

12. The process of claim 1, wherein the ionic resin is selected from the group consisting of ionic divinyl-benzene copolymer, ionic ethylvinylbenzene-divinyl-benzene copolymer, ionic styrene-divinyl-benzene copolymer, and ionic polystyrene.

13. The process of claim 1, wherein the non-ionic resin is selected from the group consisting of non-ionic divinyl-benzene copolymer, non-ionic ethylvinylbenzene-divinyl-benzene copolymer, non-ionic styrene-divinyl-benzene copolymer and non-ionic polystyrene.

14. The process of claim 1, wherein the high purity isoflavone enriched fraction has a purity in a range of greater than 90%.

15. A process for purifying isoflavones from soybeans, the process comprising:
   subjecting an aqueous solution of hexane defatted soybean flakes to an ionic adsorptive chromatographic step, thus producing an isoflavone enriched fraction; and
   subjecting the isoflavone enriched fraction to a non-ionic adsorptive chromatographic step, thus producing a high purity isoflavone enriched fraction having a purity in a range of 70% to 100%;
   wherein the isoflavones in the high purity isoflavone enriched fraction originate from the soybeans.

16. A process for isolating isoflavones, the process comprising:
   obtaining soy whey from crushed or ground soybeans;
   placing the soy whey in contact with an ionic resin such that the isoflavones are retained by the ionic resin;
   washing the first resin with a solvent such that the isoflavones are eluted from the ionic resin in an effluent;
   placing the effluent comprising the isoflavones in contact with a second resin such that the isoflavones are retained by the second resin;

washing the second resin with a second solvent such that the isoflavones are eluted from the second resin in a second effluent; and wherein said second effluent has an isoflavone purity in the range of 70% to 100%;

wherein the isoflavones originate from the crushed or ground soybeans.

17. The process of claim 16, wherein the solvent comprises an alcohol and the second solvent comprises an alcohol.

18. The process of claim 1, wherein the soy solubles comprise at least 0.9 percent isoflavones by weight.

* * * * *